Figure 1:
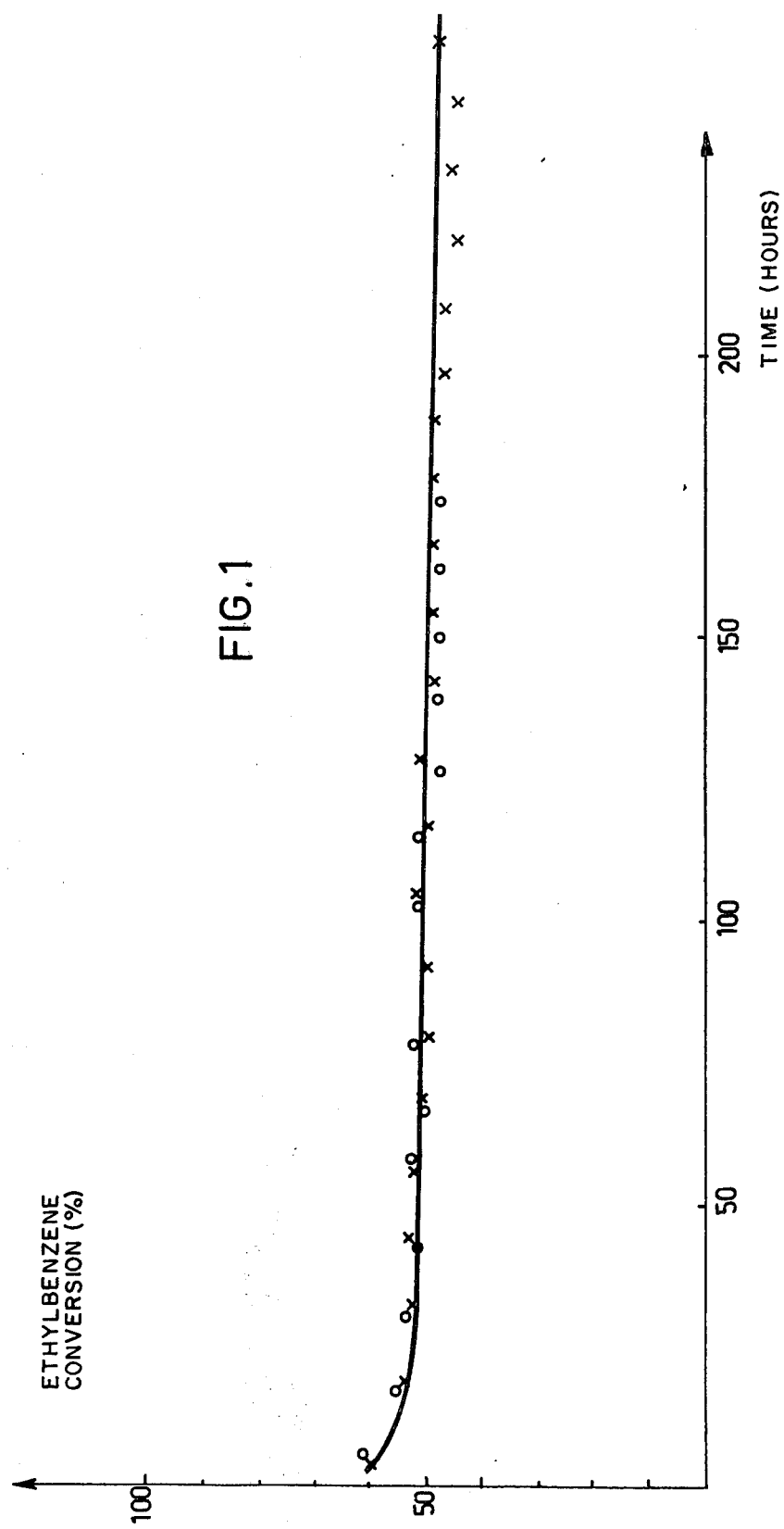

United States Patent [19]

Weisang et al.

[11]  4,116,870

[45] * Sep. 26, 1978

[54] CATALYSTS FOR THE HYDROTREATMENT OF HYDROCARBONS AND PROCESSES FOR THE UTILIZATION OF SAID CATALYSTS

[75] Inventors: Joseph Edouard Weisang; Philippe Engelhard, both of Le Havre, France

[73] Assignee: Compagnie Francaise de Raffinage, Paris, France

[ * ] Notice: The portion of the term of this patent subsequent to Aug. 10, 1993, has been disclaimed.

[21] Appl. No.: 690,908

[22] Filed: May 28, 1976

[30] Foreign Application Priority Data

May 28, 1975 [FR] France ................... 75 16703

[51] Int. Cl.$^2$ .................. B01J 27/04; B01J 27/08; B01J 27/10
[52] U.S. Cl. .................... 252/439; 252/441; 252/442; 208/136; 208/139; 260/668 A
[58] Field of Search .................. 252/441, 466 PT, 439

[56] References Cited

U.S. PATENT DOCUMENTS

| | | | |
|---|---|---|---|
| 2,957,819 | 10/1960 | Haensel | 208/139 X |
| 3,002,920 | 10/1961 | Porter et al. | 252/466 PT X |
| 3,700,588 | 10/1972 | Weisang et al. | 208/139 |
| 3,806,446 | 4/1974 | Hayes | 252/441 X |
| 3,974,097 | 8/1976 | Weisang et al. | 252/441 X |
| 4,048,099 | 9/1977 | Hayes | 252/439 |

*Primary Examiner*—Patrick Garvin
*Attorney, Agent, or Firm*—Curtis, Morris & Safford

[57] ABSTRACT

A catalyst useful for the hydrotreatment of hydrocarbons comprising, on a refractory inorganic oxide support, the following metals:

(a) from 0.02 to 2% of at least one platinum metal;

(b) from 0.02 to 2% of at least one metal belonging to the group consisting of zirconium, titanium, and tungsten;

(c) from 0.02 to 2% tin.

This catalyst is preferably halogenated, typically with chlorine, from 0.4 to 2%.

Catalysts according to this invention are particularly useful for isomerization of a charge of alkylaromatic hydrocarbons, and particularly those having eight carbon atoms. The preferred isomerization catalyst is a platinum, tin and zirconium trimetallic catalyst halogenated with chlorine approximately from 1 to 2% based on the total catalyst weight.

Said catalysts are also useful for hydroreforming and aromatizing being surprisingly superior for all these types of reactions.

24 Claims, 3 Drawing Figures

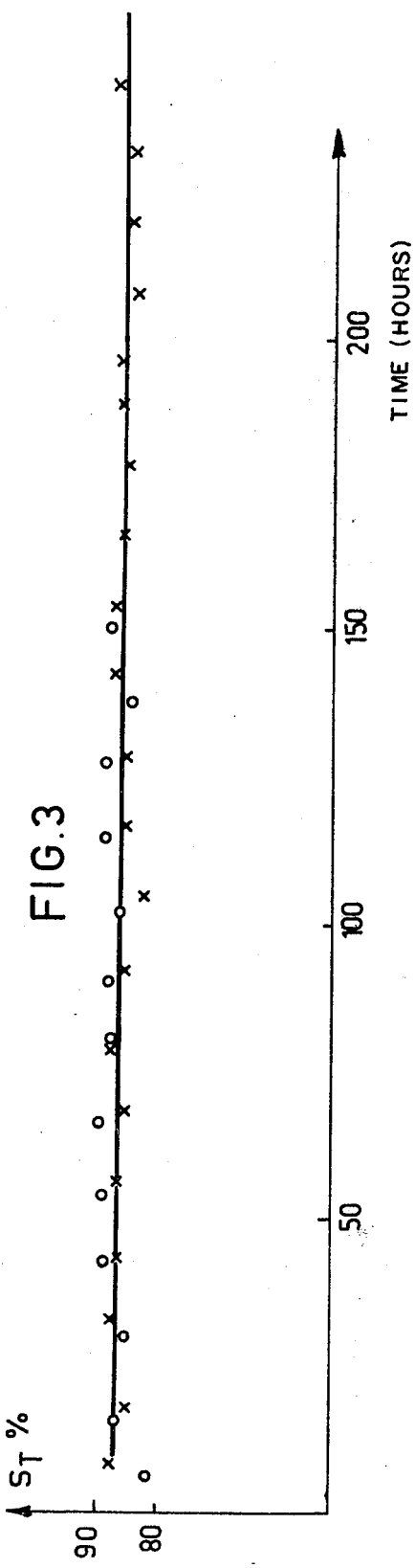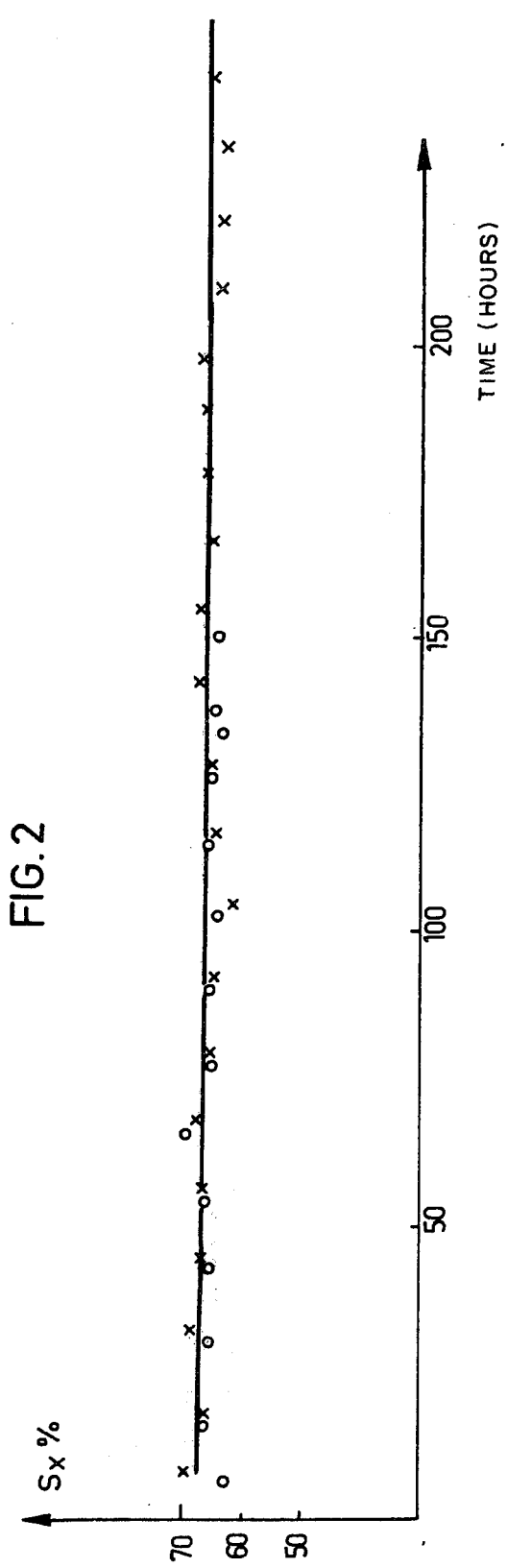

CATALYSTS FOR THE HYDROTREATMENT OF HYDROCARBONS AND PROCESSES FOR THE UTILIZATION OF SAID CATALYSTS

The present application is a continuation-in-part of application Ser. No. 525,675, filed Nov. 20, 1974, now U.S. Pat. No. 3,974,097 issued Aug. 10, 1976, the disclosure of which is hereby fully incorporated by reference.

The additional subject matter of the present application particularly relates to hydrotreatment of hydrocarbon charges, namely, the isomerization of alkylaromatic hydrocarbons.

It will be recalled that said main patent relates to catalysts for the hydrotreatment of hydrocarbons comprising a refractory mineral oxide carrier which has acid sites and contains a halogen element present in combined form, said catalyst being characterized by the fact that it comprises the following metals, in the free or combined state:

(a) From 0.02 to 2%, and preferably from 0.10 to 0.70%, on the basis of the total weight of the cataysr, of at leat one metal from the platinum group;

(b) from 0.02 to 2%, and preferably from 0.02 to 0.60%, based on the total catalyst weight, of at least one metal from the group consisting of zirconium, titanium and tungsten;

(c) from 0.02 to 2%, and preferably from 0.05 to 1%, based on the total catalyst weight, of tin. Said percentages being calculated with respect to the elemental form.

The carrier of said catalysts preferably has a specific surface greater than 15 $m^2/g$. Said carrier may, for example, be an alumina of a specific surface comprised between 100 and 350 $m^2/g$. It further has a specific pore volume greater than 0.1 $cm^3/g$.

The halogen which is contained in the carrier is preferably chlorine, at a concentration of 0.4 to 2% by weight, based on the total weight of the catalyst, and preferably from 0.5 to 1.6%.

U.S. Pat. No. 3,974,097 issued Aug. 10, 1976 also described a process for the preparation of said catalysts, the utilization of these catalysts in the hydroreforming of a charge of hydrocarbons having a boiling point comprised between 35° and 250° and a low sulfur content, and their utilization in the aromatization of hydrocarbon charges.

Applicants have discovered that these catalysts lend themselves particularly well to a refining process other than hydroreforming and aromatization.

Consequently, the invention according to the present application is the utilization of catalysts of U.S. Pat. No. 3,974,097 issued Aug. 10, 1976 in the isomerization of alkylaromatic hydrocarbons.

This process is similar to hydroreforming. The reactions which it entails also take place in hydroreforming, accompanied by other reactions such as hydrogenation-dehydrogenation, for example, or dehydrocyclization.

The reaction conditions employed in these various processes industrially are not the same. Nor are, as a rule, the catalysts employed in carrying out said reactions necessarily the same.

A great many catalysts are known for the isomerization of alkylaromatic hydrocarbons, for example. Many of them comprise a porous alumina or aluminosilicate carrier on which is deposited a so-called "noble" metal such as platinum, whether or not associated with other metals, among which may be cited iridium, tin, rhenium, lead, and germanium. It is also known to associate one or more "non-noble" metals on such a carrier, such as the metals from groups I$b$, II$b$, V$b$ or VI$b$ of the periodic table elements.

The isomerization of alkylaromatic hydrocarbons is an operation that is carried out at a temperature slightly below the temperatures employed in hydroreforming. It is generally carried out below 500° C. and above 350° C., for example, between 430° C. and 480° C., at a pressure on the order of 25 to 35 bars. The space velocity (v/v/hr) of the hydrocarbon charge, measured in the liquid state, usually is in the neighborhood of 1 to 2. The operation is carried out in the presence of hydrogen, the molar ratio of hydrogen to hydrocarbons ranging approximately from 8 to 10.

It is not rare that a good catalyst of one of the processes is an average or poor performer when it is employed in one of the other processes. Under the circumstances, it is remarkable that the catalysts whose general formula is described in the main patent are good catalysts in any of the three processes, hydroreforming, aromatization and isomerization. However, while for the aromatization of hydrocarbons having six or seven carbon atoms no adjustment of the catalytic formula is necessary, in the case of the isomerization of alkylaromatic hydrocarbons, and particularly of those having eight or more carbon atoms, the halogen content must be somewhat higher than the halogen contents used with reforming and aromatization catalysts. Thus, halogen contents ranging approximately from 1 to 2%, based on the total catalyst weight, are preferably employed.

Applicants have found that formulas containing platinum, tin and zirconium are particularly advantageous for the isomerization reaction.

For the applications in accordance with the present invention, the catalysts may, prior to their utilization, be advantageously subjected to a reduction and possibly a presulfurization, as described in U.S. Pat. No. 3,974,097 issued Aug. 10, 1976.

EXAMPLE 1

This example illustrates the use of catalysts according to the present invention in the isomerization of an aromatic hydrocarbon having eight carbon atoms, namely, ethylbenzene. Since ethylbenzene is not as much in demand as xylenes, it is advantageous to isomerize it so as to convert it to xylenes.

The catalytic test is conducted under the following conditions:

Temperature: 450° C.
Pressure: 30 bars
Space velocity (v/v/hr): 2
Ratio of $H_2$ to charge: 5

The charge is ethylbenzene, which by isomerization gives xylenes and precursors of xylenes such as ethylcyclohexane, dimethylcyclohexanes, methylethylcyclopentanes, etc. The volume of catalyst placed in the reactor is 40 $cm^3$.

The carrier of the catalyst is an alumina identical to the one described in U.S. Pat. No. 3,974,097.

The catalyst comprises 0.37% platinum, 1.35% chlorine, 0.19% tin and 0.15% zirconium. It is tested over several tens of hours. The samples taken from the effluent give information on the ethylbenzene conversion (that is to say, the percentage of ethylbenzene converted in relation to ethylbenzene introduced), which is indicative of the activity of the catalyst for isomerization;

the selectivity for xylenes, Sx; and the overall selectivity, St, for xylenes and precursors of xylenes.

The result of these measurements are presented in the accompanying FIGS. 1, 2 and 3, which illustrate the evolution of the conversion of ethylbenzene and the two selectivities Sx and St (the representative points of these catalysts being marked by a cross, $x$) as a function of time.

FIG. 1 shows that after a slight decrease in catalyst activity at the start of operation, which is normal, the activity of the catalyst becomes stabilized, ethylbenzene conversion being in the neighborhood of 50%.

FIGS. 2 and 3 show that the catalysts in accordance with the invention are highly selective for xylenes and their precursors, there being practically no variation over the 300 hours of the test. Sx fluctuates between 65 and 70%, St between 85 and 90%.

The catalysts are therefore very good isomerization catalysts.

By way of a comparative example, an identical test was run with a catalyst containing only platinum and chlorine deposited on an identical support, the composition of the catalyst being as follows:

Platinum: 0.35 wt. %
Chlorine: 1.35 wt. %

In FIGS. 1, 2 and 3, the points representative of the behavior of these control catalysts are marked with the symbol $o$.

When these two catalysts are compared, it is seen that they are substantially equivalent in terms of conversion and selectivity throughout the duration of the test.

However, the applicants have observed that there is a great deal of difference in the amount of carbon deposited on the two catalysts after about 350 hours of operation. In the case of the catalyst containing platinum, tin and zirconium according to the present invention, the rate of carbon deposition is considerably less than 1 wt. % (about 0.8 wt %) whereas in the case of the conventional catalyst containing only platinum, the rate of carbon deposition is higher than 2 wt. %.

From the industrial point of view, it thus follows that while the catalysts in accordance with the main patent are substantially equivalent to the conventional catalysts in terms of conversion and selectivity during the first few hundred hours of operation, they need to be regenerated less frequently than the conventional catalysts, which is a considerable advantage in the operation of the unit.

EXAMPLE 2

This example illustrates the utilization of the catalyst, already used in example 1, in the isomerization of hydrocarbon charges containing alkylaromatic hydrocarbons having eight carbon atoms.

Table 1 shows the results of tests performed over 6 hours on charges whose composition is given in that table.

TABLE 1

| Composition of charge (wt. %) | | | Reaction Conditions | | | | Composition of effluent (wt %) | | | | | | | |
|---|---|---|---|---|---|---|---|---|---|---|---|---|---|---|
| Ethyl-benzene (eb) | Meta-xylene (mx) | Ortho-xylene (ox) | v/v/hr | Temp. °C | Relative total pressure (bars) | $H_2$/HC | Light HC* | Toulene | eb | px | mx | ox | Intermediates HC** | Heavy HC*** |
| 13.50 | 64.50 | 21.40 | 2 | 480 | 35 | 5 | 4.95 | 3.34 | 8.68 | 13.33 | 39.47 | 16.98 | 12.85 | 0.39 |
| 13.50 | 64.50 | 21.40 | 2 | 480 | 25 | 10 | 2.46 | 2.26 | 11.10 | 10.34 | 49.37 | 19.68 | 4.56 | 0.24 |
| 13.50 | 64.50 | 21.40 | 2 | 440 | 25 | 5 | 3.5 | 1.23 | 9.85 | 7.59 | 48.39 | 18.01 | 11.30 | 0.14 |
| 17.45 | 61.30 | 20.15 | 1.5 | 460 | 30 | 7.5 | 3.86 | 2.16 | 11.39 | 10.21 | 44.23 | 17.61 | 10.39 | 0.15 |
| 17.45 | 61.30 | 20.15 | 1.5 | 460 | 30 | 7.5 | 3.09 | 2.38 | 11.65 | 10.38 | 44.74 | 18.15 | 9.28 | 0.34 |
| 19.8 | 59.7 | 19.6 | 1 | 480 | 25 | 10 | 3.69 | 4.14 | 13.81 | 13.59 | 42.83 | 18.46 | 3.24 | 0.24 |
| 19.8 | 59.7 | 19.6 | 1 | 440 | 25 | 5 | 4.41 | 2.25 | 11.95 | 12.72 | 41.40 | 17.38 | 9.5 | 0.38 |
| 19.8 | 59.7 | 19.6 | 2 | 480 | 25 | 5 | 1.90 | 2.78 | 15.85 | 10.23 | 46.75 | 18.96 | 2.76 | 0.75 |
| 19.8 | 59.7 | 19.6 | 2 | 480 | 35 | 10 | 3.43 | 1.30 | 13.74 | 8.64 | 46.36 | 16.54 | 9.92 | 0.08 |

The results presented in this table show that the catalysts in accordance with the main patent have a goodisomerizing activity without causing considerable cracking. (Cracking is largely characterized by the quantityof light products obtained).

*"Light HC" means hydrocarbons other than toluene having seven or fewer carbon atoms.
**"Intermediate HC" means the precursors of xylenes.
***"Heavy HC" means hydrocarbons having nine or more carbon atoms, other than precursors of xylenes.

EXAMPLE 3

In this example, a catalytic test is run with a formula containing:

0.38% platinum
0.19% tin
0.15% zirconium
1.81% chlorine

The carrier is an alumina identical to the one described in U.S. Pat. No. 3,974,097 issued Aug. 10, 1976. The principal operating parameters are:

Temperature: 450° C.
Pressure: 30 bars
Space velocity (v/v/hr): 2
Molar ratio of hydrogen to hydrocarbons: 5

The hydrocarbon charge which is made to undergo isomerization is a mixed charge having a composition that is variable with time and containing precursors of xylenes and ethylbenzene, these products being the only ones capable of giving, by isomerization, the xylenes sought. The rest of the charge is composed of orthoxylene (about 20 wt. %) and metaxylene (about 60 wt. %).

Table 2 presents the results of this test, in which about 20 ppm of water and 10 ppm of chlorine were injected with the charge so as to maintain the chlorine content of the catalyst with time.

It is apparent from this table that the performance of this formula is very good.

TABLE 2

| Time of catalyst (hours) | Composition of charge | | | Partial composition of effluent (wt. %)*** | | | |
|---|---|---|---|---|---|---|---|
| | Intermediates (%) | Ethylbenzene (%) | Ethylbenzene Conversion | C7– fraction* | C9+ fraction** | Aromatics with C8 | Paraxylene |
| 284 | 4.96 | 17.68 | 41.9 | 5.35 | 1.13 | 84.7 | 17.0 |
| 292 | 4.96 | 17.68 | 38.7 | 4.84 | 0.82 | 86.2 | 16.2 |
| 356 | 0 | 22.45 | 43.7 | 4.95 | 1.02 | 88.0 | 15.83 |
| 380 | 7.35 | 16.77 | 35.4 | 5.78 | 1.02 | 83.96 | 16.17 |
| 388 | 7.35 | 16.77 | 36.7 | 5.64 | 1.08 | 84.88 | 15.62 |
| 404 | 0 | 19.11 | 36.6 | 4.64 | 1.02 | 87.4 | 17.97 |
| 412 | 0 | 19.11 | 37.2 | 3.74 | 0.90 | 89.2 | 17.64 |
| 493 h 30 | 0 | 22.45 | 40.3 | 4.63 | 0.79 | 88.65 | 16.3 |
| 501 h 30 | 0 | 22.45 | 37.55 | 5.57 | 1.16 | 87.3 | 16.0 |
| 517 h 30 | 9.75 | 16.25 | 37.85 | 5.51 | 1.15 | 83.97 | 16.73 |
| 524 h 30 | 9.75 | 16.25 | 32.61 | 6.01 | 0.92 | 83.55 | 16.10 |
| 541 h 30 | 0 | 22.45 | 40.44 | 4.51 | 1.18 | 88.8 | 16.96 |
| 549 h 30 | 0 | 22.45 | 39.55 | 4.74 | 1.17 | 88.3 | 16.0 |

*C7– fraction = formed of hydrocarbons having seven or fewer carbons
**C9+ fraction = formed of hydrocarbons having nine or more carbons
***The rest of the effluent is formed of naphthenes and paraffins having eight carbons

We claim:
1. A catalyst for the hydro-treatment of hydrocarbons comprising a refractory inorganic oxide support having acid sites, having between about 0.4 and 2% of halogen present in combined form with other catalyst components, and consisting essentially of the following on said support:
   (a) about 0.02 to 2% of at least one platinum-metal ingredient,
   (b) about 0.02 to 2% of at least one additional zirconium, or titanium ingredient, and
   (c) about 0.02 to 2% of a tin ingredient; said weight percentages being calculated with respect to the respective elemental forms of said components and based on the total weight of the catalyst.

2. A catalyst according to claim 1, wherein said ingredients are only of tin, of platinum and of one additional ingredient.

3. A catalyst according to claim 2, wherein said ingredients comprise:
   (a) 0.1 to 0.7% of at least one platinum-metal ingredient,
   (b) 0.02 to 0.60% of said additional ingredient, and
   (c) 0.05 to 1.00% of said tin ingredient.

4. A catalyst according to claim 2, wherein the halogen content is between 0.5 and 1.6%, referred to the total weight of the catalyst.

5. A catalyst according to claim 2, wherein said additional ingredient is only of zirconium.

6. A catalyst according to claim 2, wherein said additional ingredient is only of titanium.

7. A catalyst according to claim 6, wherein the halogen is chlorine.

8. A catalyst according to claim 5, wherein the halogen is chlorine.

9. A catalyst according to claim 7, characterized furthermore by the fact that the support is an alumina whose specific surface is between 100 and 350 m²/g.

10. A catalyst according to claim 8, characterized furthermore by the fact that the support is an alumina whose specific surface is between 100 and 350 m²/g.

11. A catalyst according to claim 1, wherein the additional ingredient is of zirconium.

12. A catalyst according to claim 11, wherein the zirconium ingredient has been deposited only essentially on the surface of said support.

13. A catalyst according to claim 12, wherein said support has a specific surface of more than 15 m²/g and a specific pore volume of more than 0.1 cm³/g.

14. A catalyst according to claim 13, wherein said ingredients are only of tin, of platinum and of zirconium, and said halogen is chlorine.

15. A catalyst according to claim 14, characterized furthermore by the fact that the support is an alumina whose specific surface is between 100 and 350 m²/g.

16. A catalyst according to claim 15, wherein the halogen content is between 0.5 and 1.6, referred to the total weight of the catalyst.

17. In a process for manufacturing a hydro-treatment catalyst having a porous refractory inorganic oxide support with a specific surface between 15 and 350m²/g, with a specific pore volume greater than 0.1cm³/g and with at least a slightly acid character, incorporating onto said support a halogen in a form combined with at least one component of the catalyst in the amount of between 0.4 and 2% and the following:
   (a) about 0.02 to 2% of at least one platinum-metal ingredient,
   (b) about 0.02 to 2% of at least an additional ingredient;
   (c) about 0.02 to 2% of a tin ingredient, said weight percentages being calculated with respect to the respective elemental forms of said components and based on the total weight of the catalyst,
   and comprising at least one impregnation of the support by at least one solution containing at least one of an additional ingredient, a platinum-metal ingredient, or a tin ingredient,
   the improvement wherein said additional ingredient is of zirconium and the incorporation of said ingredients onto said support comprises at least one of the impregnation solutions which contain either cations or anions containing zirconium.

18. A process according to claim 17, wherein any depositing of zirconium and tin ingredients is effected before the depositing of any of the platinum metal ingredients.

19. A process according to claim 18, wherein all the ingredients of the catalyst are impregnated onto the support by deposit from solution and, before the depositing of any platinum-metal ingredients and after the depositing of any of the other ingredients, the support is treated with a solution of hydrochloric acid.

20. A process according to claim 19 comprising furthermore after the depositing of the ingredients on the support by impregnation, drying of the catalyst at about 100° C. and calcining at about 500° C., and reduction by hydrogen.

21. A process according to claim 20 further comprising after calcining a pre-sulfurizing of the catalyst.

22. A process according to claim 21, wherein the reduction and the pre-sulfurizing are effected simultaneously.

23. A process according to claim 17, wherein said platinum-metal ingredients are only of platinum.

24. A process according to claim 23, consisting essentially of the foregoing specific ingredients and said halogen being only chlorine and said support being only alumina.

* * * * *